United States Patent [19]

Schofield

[11] Patent Number: 4,863,861
[45] Date of Patent: Sep. 5, 1989

[54] BIOCHEMICAL PROCESS TO PRODUCE CATECHOL OR 1,2-DIHYDROXYCYCLOHEXA-3,5-DIENE COMPOUND(S)

[75] Inventor: John A. Schofield, Sittingbourne, England

[73] Assignee: Shell Oil Company, Houston, Tex.

[21] Appl. No.: 68,491

[22] Filed: Jul. 1, 1987

[30] Foreign Application Priority Data

Jul. 8, 1986 [GB] United Kingdom ............... 8616612
Jul. 8, 1986 [GB] United Kingdom ............... 8616613
Jul. 8, 1986 [GB] United Kingdom ............... 8616614

[51] Int. Cl.$^4$ .................... C12P 7/02; C07C 35/14
[52] U.S. Cl. .................................... 435/155; 435/877
[58] Field of Search ............................. 435/155, 877

[56] References Cited

U.S. PATENT DOCUMENTS 4,508,822  4/1985  Taylor ................................. 435/155

FOREIGN PATENT DOCUMENTS 76606  4/1983  European Pat. Off. .

OTHER PUBLICATIONS

Gibson et al., *Biochemistry*, 7 (7), 1968, p. 2653.
Gibson et al., *Biochemistry*, 9 (7), 1980, p. 1631.
Gibson et al., *Biochemistry*, 7 (11), 1978, p. 3795.

*Primary Examiner*—Herbert J. Lilling

[57] ABSTRACT

A process for the preparation of a catechol and/or a compound comprising a 1,2-dihydroxycyclohexa-3,5-diene ring, which comprises growing a microorganism in the presence of a carbon source, the microorganism being capable of converting the corresponding aromatic compound into the catechol and/or the compound comprising a 1,2-dihydroxycyclohexa-3,5-diene ring; and supplying the corresponding aromatic compound to the microorganism; characterized in that the carbon source is molasses.

4 Claims, No Drawings

BIOCHEMICAL PROCESS TO PRODUCE CATECHOL OR 1,2-DIHYDROXYCYCLOHEXA-3,5-DIENE COMPOUND(S)

This invention relates to a biochemical process for the production of catechols and/or dihydrodiols.

Microbial oxidations of benzene are well known. For example, the ability of the organism *Pseudomonas putida* to metabolise benzene and certain substituted benzenes to their corresponding dihydrodiols, catechols and further degradation products is known from the work of Gibson et al, Biochemistry, 7(7), 1968, p. 2653; and Biochemistry, 9(7), 1970, p. 1631. Thus, for benzene, the metabolism is believed to follow an enzyme-catalysed reaction sequence in which benzene is converted by a dioxygenase to cis-1,2-dihydroxy-cyclohexa-3,5-diene (sometimes known as "cis-benzene glycol" or "benzene dihydrodiol") which under the action of a diol dehydrogenase is converted to catechol, which is further enzymatically converted to further degradation products. A related pathway is believed to occur for toluene metabolism using *Pseudomonas putida* (Gibson et al, Biochemistry, 9(7), 1970, p. 1627).

While the dihydrodiols and catechols would be useful products, it has been found difficult to control the reaction to give sufficient yield of the desired compound as a pure product. European Pat. No. 76606 describes one attempt to produce an efficient process for the preparation of useful products.

We have now found a particular carbon source which enables the production of useful products surprisingly efficiently and cheaply.

Accordingly, the present invention provides a process for the preparation of a catechol and/or a compound comprising a 1,2-dihydroxycyclohexa-3,5-diene ring, which comprises growing a microorganism in the presence of a carbon source, the microorganism being capable of converting the corresponding aromatic compound into the catechol and/or the compound comprising a 1,2-dihydroxycyclohexa-3,5-diene ring; and supplying the corresponding aromatic compound to the microorganism; characterized in that the carbon source is molasses.

The molasses may be a sugar cane molasses, a sugar beet molasses, corn molasses, citrus molasses, grain sorghum molasses, sorgo molasses or wood molasses. Such products are described in Kirk-Othmer, "Encyclopedia of Chemical Technology", Second Edition, Interscience Publishers, New York, under the entry entitled "MOLASSES" in Volume 13, pages 613 to 633. Advantageously the molasses is a sugar cane molasses or a sugar beet molasses. Sugar cane molasses include first molasses, second molasses, final or blackstrap molasses, refiners' molasses, high-test molasses and distillers' solubles. Sugar beet molasses include final molasses, discard molasses and Steffen's waste.

Sugar cane molasses are the most preferred molasses and the most readily available form of sugar cane molasses in large quantities is final or blackstrap molasses.

The success of molasses in the process of the invention is particularly surprising as a sugar such as glucose (which is a constituent of molasses) acts as a repressor of enzyme synthesis and, when employed as carbon source in the above process, gives a very low level of production of the desired compounds. Since molasses is a comparatively cheap material, it has commercial advantages as a carbon source.

The aromatic compound used as feedstock may for example be benzene, leading to the production of catechol and/or cis-1,2-dihydroxy-cyclohexa-3,5-diene. However a preferred starting material is fluorobenzene leading to the production of 3-fluorocatechol and/or cis-1,2-dihydroxy-3-fluoro-cyclohexa-3,5-diene, which are useful intermediates in the production of, for example, pharmaceuticals and organo-fluorine agrochemicals. 3-Fluorocatechol is difficult to prepare chemically and is expensive. A further useful feedstock is trifluoromethyl benzene.

The microorganism may be any one which carries out the desired conversion. Suitable microorganisms include those of the genus Pseudomonas, Moraxella, Achromobacter, Bacillus, Beijerinckia, Alcaligenes, Flavobacterium, Phenylobacterium, Nocardia, Micrococcus, Arthrobacter, Corynebacterium and Aeromonas. Particularly preferred are *Pseudomonas putida* strains.

The particular microorganism chosen will of course depend on the desired product. Different microorganisms are available which can produce primarily a catechol, primarily a dihydrodiol, or a mixture. The optimal microorganism will also of course vary depending on which aromatic compound is chosen as feedstock.

One preferred microorganism capable of using benzene, fluorobenzene or trifluoromethylbenzene as feedstock is that deposited with effect from 6th Dec. 1985 with the National Collection of Industrial Bacteria, Torrey Research Station, Aberdeen, Scotland and assigned the numerical designation NCIB 12190 and referred to herein as "*P.putida* NCIB 12190". In addition, mutants of this microorganism are very useful. Further particularly suitable microorganisms are those described in European Pat. No. 76606, e.g. mutants of *Pseudomonas putida* NCIB 11767 or *Pseudomonas putida* NCIB 11680.

Our copending Application (our ref K 1033) describes and claims *Pseudomonas putida* NCIB 12190 and its mutants. Certain of these microorganisms are constitutive of the necessary enzymes in the preparation of certain catechols and/or dihydrodiols.

*Pseudomonas putida* NCIB 12190 was isolated from a soil sample taken from ground within the Shell Refinery in Pernis, Rotterdam.

Mutant strains of *Pseudomonas putida* NCIB 12190 capable of accumulating cis-dihydroxycyclohexadiene or catechol or their fluorinated analogues when cultured in the presence of benzene or fluorobenzene are obtainable by a selection procedure which comprises mutating *Pseudomonas putida* NCIB 12190 by chemical or physical means, allowing the mutated bacteria to grow in the presence of a carbon source, exposing the grown bacteria to benzene or fluorobenzene and selecting those mutant strains of *Pseudomonas putida* which have accumulated cis-dihydroxycyclohexadiene or catechol or their fluorinated analogues.

Suitable components of the medium employed for the biochemically catalysed oxidation of an aromatic compound may be selected to optimise the conversion to the desired products and to minimize breakdown to muconic acid and further breakdown products. A suitable medium is a nitrogen-free salts medium, an example of which is given below.

The product compound or compounds may be recovered from the resulting fermentation broth by any suitable means, such as by solvent extraction, or by adsorption onto granulated charcoal, followed by stripping with a suitable solvent with further purification as necessary dependent on the intended use of the product.

As a further preferred feature, especially when operating with benzene as a starting material, a protein synthesis inhibitor may be included in the culture, so as to inhibit the synthesis of breakdown enzymes and thus enhance the accumulation of products in the reaction mixture. A preferred protein synthesis inhibitor is chloramphenicol, but other bacteriostatic antibiotics, such as tetracycline, can be used which inhibit growth but do not kill the cells employed in the process. The need to employ a protein synthesis inhibitor is dependent on the starting material and the ease with which the degradative steps beyond the desired products tend to occur. Thus while such an inhibitor is preferred for use with benzene as starting material, it has been found not to be necessary in the case of flurobenzene as starting material.

In preferred embodiments of the process described above, no induction of enzymes is necessary to give a culture which can produce the desired product. Thus the initial growth using carbon sources such as benzene and toluene is avoided, which can simplify reactor design, as fermenters able to prevent the escape of benzene will not be needed. Further, the presence of unwanted chemicals in the reaction mixture is avoided.

*Pseudomonas putida* NCIB 12190 has been characterised and identified by the NCIB as follows:

Tests were at 25° C. and growth was on LAB M Nutrient Agar unless otherwise stated.

Cell Morphology

After growth for 24 hours at 30° C. on succinate agar and transfer to Nutrient broth+0.75% w agar, by phase contrast at ×630 magnification the cells are small short rods or cocci in clusters.

Gram Negative

Spores —

Motility +

Colonial Morphology

After 48 hours growth, colonies are round, regular, entire, smooth, opaque, low convex, off-white and less than 1 mm in diameter.

Growth on Glucose Peptone Water Sugars

37° C. +

41° C. —

Catalase +

Oxidase, Kovacs +

O-F glucose Oxidative

"O-F glucose" was performed using the oxidation-fermentation medium of Hayward and Hodgkiss, *J. Gen. Microbiol.*, 26, (1961), pp. 133–140, supplemented with 1% w filter-sterilised D-glucose. A tube sample was inoculated and incubated for 14 days.

*Pseudomonas putida* NCIB 12190 can conveniently be stored on nutrient agar slopes at 4° C., or as a freeze-dried material.

The UV mutant of *Pseudomonas putida* NCIB 12190 described in Example 1 had the same characteristics as those described above, with the exception of motility-negative.

The following examples illustrate the invention.

Colorimetric determination of cis-dihydroxycyclohexadienes and catechols

The methods of Friestad et al., Analytical Chemistry 41, 1969, pp. 1750–1754 was used. Solutions to be tested for catechols were mixed with an equal volume of 3-methyl-2-benzothiazolinone hydrazone hydrochloride (0.05% w/v in water) and an equal volume of ceric ammonium sulphate (0.2% w/v in 0.4% w/v sulphuric acid). Optionally, a borate-NaOH-EDTA buffer was added after a few minutes, as descried by Friestad et al. The intensities of the colours which developed were compared visually or, alternatively, were measured spectrophotometrically at 520 nm. cis-Dihydroxycylohexadienes do not produce colours under these conditions. Therefore a second sample of each test solution was acidified with sulphuric or hydrochloric acid before the colour test, to convert the dihydroxycyclohexadienes quantitatively to phenols. The difference in colour intensity given by the acidified and unacidified samples is indicative of the content of dihydroxycyclohexadienes.

Media Used

The compositions of two of the media used in the following examples are given below in Table 1.
ASM—minimal salts medium
NFSM—nitrogen-free salts medium

TABLE 1

| | amounts per liter | |
|---|---|---|
| | ASM | NFSM |
| $Na_2HPO_4$ | 0.866 g | 7 g |
| $K H_2PO_4$ | 0.531 g | 3 g |
| $NH_4Cl$ | 0.535 g | — |
| $K_2SO_4$ | 0.174 g | 0.174 g |
| $MgSO_4.7H_2O$ | 0.037 g | 0.037 g |
| $CaCl_2.2H_2O$ | 0.00735 g | 0.00735 g |
| TK3 (T/E) (see below) | 1.0 ml | 1.0 ml |
| $FeSO_4.7H_2O$(0.1 M) | 0.2 ml | 0.2 ml |
| | pH 6.8 | |

Composition of TK/3 Trace Element Solution

This contained per liter the following components:
$ZnSO_4.7H_2O$ (0.288 g); $MnSO_4.4H_2O$ (0.224 g); $H_3BO_3$ (0.0618 g); $CuSO_4.5H_2O$ (0.1248 g); $Na_2MoO_4.2H_2O$ (0.0484 g); $CoCl_2.6H_2O$ (0.0476 g); KI (0.083 g); 1M $H_2SO_4$ (1 ml).

Further media used were:
dYT medium:
 16 g Bacto tryptone
 10 g Bacto yeast extract
 5 g NaCl/l
Yeast extract medium (YEM):
 10 g/l disodium succinate $0.6H_2O$
 2 g/l $(NH_4)_2SO_4$
 3 g/l yeast extract (Difco)
 0.4 g/l $MgSO_4.7H_2O$
 0.04 g/l Bacto-peptone in
 25 mM potassium phosphate buffer, final pH 7.0.

Thin layer chromatorgraphy (TLC)

Aqueous samples (5 μl) were run on Merck Kieselgel 60 F254 plates developed with 90:10:1 (v/v) n-propanol-water-formic acid. Dihydroxycyclohexadiene content was visualised under short wave uv light and catechol was detected by spraying with 2,6-dichloroquinone-4-chloroimide (2% in ethanol).

Gas chromatography (GC)

Aqueous samples (0.5 μl) were chromatographed on a Hewlett Packard 25-meter high capacity flexible silica capillary column coated with 5%-phenylmethylsilicone, using helium as carrier gas. The column was held at 130° C., and eluted compounds were detected by a flame ionisation detector.

EXAMPLE 1

The preparation of NTG mutants of P.putida NCIB 12190

*Pseudomonas putida* NCIB 12190 was grown overnight at 30° C. in dYT medium. The culture was subcultured 1/20 into 10 ml fresh dYT and incubated for a further 4 hours. The bacteria were harvested by centrifugation, washed in NFSM and again harvested by centrifugation before resuspension in NFSM (3 ml) and adjustment of the OD 600 nm to 3.0.

A 1 ml aliquot in an "Eppendorf" tube was incubated at 30° C. for 15 mins and then NTG (N-methyl-N'-nitro-N-nitrosoguanidine-5 mg/ml in dimethyl sulphoxide) added to give 50 µg/ml. The tube contents were briefly mixed and incubated at 30° C. for 15 mins. Mutation was stopped by chilling in ice, centrifugation and washing (3 times in saline-0.85% NaCl). The bacteria were diluted in saline and 0.1 ml aliquots plated out onto 100 ASM plates each including 0.05% sodium succinate. The plates were incubated at 30° for 48 hours.

After incubation, small "micro" colonies were visible on the plates, the level of succinate having been only sufficient for a small amount of growth. The plates were then exposed to benzene vapour for 24 h at 30° C. resulting in a wide variety of colony sizes visible on the plates. In an initial selection procedure, small colonies on the plates (which are small because of their inability to grow on benzene) (20-30/plate) were picked using sterile cocktail sticks into 96 well microtitre plates (Titertek) containing 50 µl ASM+0.5% sodium succinate per well. The plates were incubated overnight at 30° C. in a sealed box to prevent evaporation and the microtitre plates replicated onto square (120 mm) plates of commercial nutrient agar (Oxide) (to provide controls) using a 96 prong replicating device. The agar plates were incubated overnight and the microtitre plates were exposed to benzene vapour for 3 hours. Subsequent assay was by the colorimetric method described above. Those mutants developing the most intense colour were selected for further testing.

Candidate organisms from the initial selection procedure were received as purified cultures on agar plates and inoculated into 1.5 ml of an ASM medium (supplemented with a trace element mixture, $Fe^{2+}$-20 µm and sodium succinate-5 g/l). The cultures were grown overnight in sloping rotating test tubes at 30° C., centrifuged, the supernatants discarded and the cells resuspended in 0.25 ml supplemented ASM in test tubes arranged nearly horizontally in a tank of benzene vapor on a rocking platform at room temperature.

After a certain benzene exposure time (usually 3 and/or 5 to 6 hours) two 0.5 ml samples of each culture were withdrawn for colour testing by the colorimetric method described above. To one of these were added 10 µl of 5M HCl to convert any cis-dihydroxycyclohexadiene present into phenol. 5 µl samples were also taken for TLC analysis. After the benzene exposure, the cultures were left in air and a final TLC sample taken next day.

Two cultures of wild type *P.putida* NCIB 12190 were included in each batch tested for comparison purposes, to one of which chloramphenicol (0.1 mg/ml) had been added before exposure to benzene. Colours and TLC spots were compared and scored on an eight-point scale from − to +++. The results are given in Table 2. Reproducibility was found to be good.

TABLE 2

| | 3 hr benzene exposure | | | | 5-6 hr benzene exposure | | | |
|---|---|---|---|---|---|---|---|---|
| | Colour Test | | TLC | | Colour Test | | TLC (next day) | |
| Mutant | + acid | no acid | Diene | Catechol | + acid | no acid | Diene | Catechol |
| CONTROLS | | | | | | | | |
| NCIB 12190 | +(+) | +(+) | − | +(+) | ++ | ++ | − | + |
| NCIB 12190 + chloramphenicol | +++ | +++ | − | +++ | +++ | +++ | − | +++ |
| CIS-DIHYDROXY-CYCLOHEXADIENE PRODUCERS | | | | | | | | |
| NTG mutant E | (+) | | | | −(+) | − | (+) | − |
| NTG mutant G | (+) | −(+) | (+) | −(+) | −(+) | − | − | − |
| NTG mutant H | + | −(+) | (+) | − | + | −(+) | (+) | − |
| NTG mutant F | +(+) | −(+) | + | − | + | −(+) | + | − |
| NTG mutant I | −(+) | − | − | − | −(+) | − | − | − |
| NTG mutant J | (+) | −(+) | − | − | (+) | −(+) | − | (+) |
| NTG mutant K | ++ | | | | ++ | (+) | − | (+) |
| NTG mutant L | −(+) | − | − | − | −(+) | − | − | − |
| NTG mutant M | (+) | − | − | −(+) | + | (+) | − | − |
| CATECHOL PRODUCERS | | | | | | | | |
| NTG mutant C | ++ | | | | ++ | +++ | − | +++ |
| NTG mutant N | +++ | +++ | − | +++ | ++(+) | ++(+) | − | +++ |
| NTG mutant O | +++ | ++(−) | − | +++ | ++(+) | ++(+) | − | +++ |
| NTG mutant P | +++ | ++(−) | − | ++(+) | ++(+) | ++(+) | − | +++ |
| NTG mutant Q | ++(+) | ++(−) | − | ++(+) | ++(+) | ++(+) | − | ++(+) |
| NTG mutant A | ++ | ++ | − | +++ | ++ | ++ | − | +++ |
| NTG mutant R | +++ | +++ | − | +++ | +++ | +++ | − | ++(+) |
| NTG mutant S | | | | | ++ | ++(+) | − | ++(+) |
| NTG mutant R | | | | | ++ | ++ | − | ++(+) |
| NTG mutant U | | | | | ++ | ++ | − | ++(+) |
| NTG mutant V | | | | | ++ | ++(+) | − | +++ |

EXAMPLE 2

The use of NTG mutant F in the production of 3-fluoro-cis-1,2-dihydroxycyclohexa-3,5-diene using molasses as carbon source A medium corresponding to YEM except that it contained no succinate (pH7.0; 8 liters) was supplemented with cane molasses (240 g), and inoculated with a shake flask culture of NTG mutant F. Air was passed at a rate of 500 ml/min into the stirred mixture (500 rpm) over a period of 20 hours. During the latter 16 hours of growth, the fermenter was fed with a solution of cane molasses (500 g/l) and ammonium sulphate (50 g/l) in 25 mM phosphate buffer (pH 7.0) at a rate of 40 ml/hour. The pH of the broth was maintained at about 7.0 by addition via a monitoring system of 10% aqueous sodium hydroxide.

After 20 hours incubation, 5 liters of the broth were withdrawn and the remainder diluted with 25 mM phosphate buffer (pH 7.0; 5l) containing ammonium sulphate (5 g). The mixture was aerated under conditions of 750 ml/min; 600 rpm and fluorobenzene (0.2 ml) added. A solution of cane molasses (250 g/l) and ammonium sulphate (25 g/l) in 25 mM phosphate buffer (pH 7.0) was added at a rate of 40 ml/hour and fluorobenzene was added at a rate of 50 µl/min. Air feed and stirring were adjusted to maintain a positive (about 30%) oxygen tension. After 5 hours, the air feed was raised to 800 ml/min and maintained for a further 15 hours.

The product reached a level of greater than 9 g/l and was isolated from the broth by absorption onto charcoal. Elution of the charcoal with ether/methanol gave product 3-fluoro-cis-1,2-dihydroxycyclohexa-3,5-diene (46 g).

EXAMPLE 3 (comparative)

The use of NTG mutant F in the production of 3-fluoro-cis-1,2-dihydroxycyclohexa-3,5-diene using succinate as carbon source 8 liters of YEM were inoculated in a stirred fermenter with a 20 hour shake flask culture of NTG Mutant F grown on the same medium (50 ml). The organism was grown at aerating conditions of 500 rpm and 500 ml. air/min. for 19 hours with a continuous feed of concentrated nutrient (320 g of disodium succinate and 64 g of ammonium sulphate in 1 liter of 0.025M potassium phosphate buffer pH 7.2) at 40 ml/hour. Oxygen transfer was increased by increasing the stirrer speed to 550 rpm and the aeration rate to 700 ml air/min for 30 min and then set to conditions of 500 rpm; 600 ml air/min; equilibrium oxygen tension 30% air saturated initially).

Fluorobenzene was metered by a pump (Gilson Model 302) at 50 µl/min (100-125 mg/l equilibrium concentration in the reaction). Prior to reaction, the optical density was determined as 3.11 corresponding to a dry cell weight of 3.9 g/l. Production of 3-fluoro-cis-1,2-dihydroxycyclohexa-3,5-diene was monitored by gas chromatography and the concentration reached 2.8 g/l after 24 hr, compared with over 9 g/l reached in Example 2.

The product was absorbed on granulated charcoal and recovered from the charcoal by extraction in a Soxhlet apparatus with a mixture of diethyl ether and methanol (4:1 v/v). Evaporation of the solvent left a solid which was recrystallised from a mixture of diethyl ether and pentane to give colourless needles, m.p. 73-74° C. (decomp.).

UV Spectrum (H$_2$O): λ max 259 nm (ε 3150).
Circular dichroism (H$_2$O): λ max 255 nm (Δε-1.9).
Mass spectrum m/z 130 (15%, M+), 112 (65%), 84 (100%).
$^1$H-NMR spectrum (CDCl$_3$): δ 5.88 (1H, mult, J=10, 6.5, 6, 2 Hz; 5-C-H), 5.71 (1H, dd, J=10, 3 Hz; 6-C-H), 5.60 (1H, dd, J=11, 6.5 Hz; 4-C-H), 4.51 (1H, br. mult, J=6, 3, 2 Hz; 1-C-H), 4.29 (1H, tr, J=6, 6 Hz; 2-C-H), 2.40 (2H, br.s, O-H) p.p.m.

EXAMPLE 4

Preparation of cis-1,2-dihydroxy-3-trifluoromethylcyclohexa-3,5-diene 50 ml of a medium corresponding to YEM but with succinate replaced by molasses at 30 g/liter was inoculated with *Pseudomonas Putida* NCIB 12190 and incubated in 250 ml conical flasks on a shaker for 17 hours at 30° C. Benzotrifluoride (0.1 ml) was added, and the flask was then sealed and further incubated on a shaker at 30° C. GLC showed the presence of 0.62 g/l of the desired product.

EXAMPLE 5

Preparation of cis-1,2-dihydroxy-3-trifluoromethylcyclohexa-3,5-diene

The procedure of Example 4 was repeated using 12.7 g/l of molasses. The final concentration of the desired product was 0.55 g/l.

EXAMPLE 6 (comparative)

Preparation of cis-1,2-dihydroxy-3-trifluoromethylcyclohexa-3,5-diene

The procedure of Examples 4 and 5 was repeated using D-glucose (10 g/l) instead of molasses as carbon source. Only 0.04 g/l of the desired product was produced.

EXAMPLE 7

Preparation of cis-1,2-dihydroxy-cyclohexa-3,5-diene

A 50 ml shake flask of NTG mutant F grown for 18 hrs on a medium comprising
  molasses: 14 g/l
  yeast extract: 3 g/l
  ammonium sulphate: 2 g/l
  magnesium sulphate heptahydrate: 0.4 g/l
  Bactopeptone: 0.4 g/l
in 25 mM potassium phosphate buffer pH 7.2, was used to inoculate 7.5-8 liters of medium containing, in 25 mM potassium phosphate, pH 7.2 . . . .
  150 g: cane molasses
  24 g: yeast extract
  16 g: ammonium sulphate
  3.2 g: magnesium sulphate heptahydrate
  0.32 g: bactopeptone The culture was grown overnight at 400 rpm whilst admitting air at 400 ml/min. Temperature was controlled at 30° and the pH at 7.0±0.1 by the demand addition of dilute (1:3 0.880 to water) ammonia solution. A feed of molasses (200 g/l) and ammonium sulphate (50 g/l) was supplied at 40 mls/hr throughout the growth period which lasted 16 hrs. After this period the feed was stopped and the culture activated by raising stirrer speed and aeration rate to 600 rpm and 500 ml/min for 45 mins. Once this phase had taken place the feed of molasses and ammonium sulphate was reintroduced at the same (40 ml/hr) rate and a supply of benzene fed to the stirred culture at a rate varying between 50 and 150 μl/min. Air and stirrer rates were varied between 1000 and 500 ml/min and 800 and 600 rpm to maintain a dissolved oxygen tension of 30–50% of saturation. With the dissolved benzene maintained at 50–100 mg/l and under these conditions the accumulation of cis benzene glycol rose to 6.3 g/l in 24 hours as measured by GLC.

I claim:

1. A process for the preparation of a catechol and/or a 1,2-dihydroxycyclohexa-3,5-diene ring, which comprises growing a strain of *Pseudomonas putida* microorganism in the presence of a carbon source, the microorganism being capable of converting the corresponding aromatic compound selected from the group consisting of benzene, fluorobenzene and trifluoromethylbenzene into the catechol and/or the compound comprising a 1,2-dihydroxyclyclohexa-3,5-diene ring; and supplying the corresponding aromatic compound to the microorganism; said process characterized in that the carbon source is molasses.

2. A process as claimed in claim 1, in which the microorganism is *Pseudomonas putida* NCIB 12190 or a mutant thereof.

3. A process as claimed in claim 1, in which the microorganism is a mutant of *Pseudomonas putida* NCIB 11767 or *Pseudomonas putida* NCIB 11680.

4. A process as claimed in any one of claims 1, 2 or 3, in which the molasses is a sugar beet or sugar cane molasses.

* * * * *